United States Patent [19]
Daikuzono

[11] Patent Number: 5,139,495
[45] Date of Patent: Aug. 18, 1992

[54] BENT AND TAPERED LASER LIGHT EMITTING PROBE

[75] Inventor: Norio Daikuzono, Chiba, Japan

[73] Assignee: S. L. T. Japan Co., Ltd., Tokyo, Japan

[21] Appl. No.: 464,113

[22] Filed: Jan. 12, 1990

[30] Foreign Application Priority Data

Jan. 17, 1989 [JP] Japan .................................. 1-8273

[51] Int. Cl.$^5$ ............................................. A61B 17/32
[52] U.S. Cl. ....................................... 606/17; 128/398
[58] Field of Search ................................ 128/395–398; 606/13–16, 2–8

[56] References Cited

U.S. PATENT DOCUMENTS

| | | | |
|---|---|---|---|
| 2,056,990 | 10/1936 | Symonds | 128/398 |
| 2,186,143 | 1/1940 | Neugass | 128/398 |
| 3,834,391 | 9/1974 | Block | 128/398 |
| 4,126,136 | 11/1978 | Auth et al. | 606/16 |
| 4,233,493 | 11/1980 | Nath | 606/16 |
| 4,273,127 | 6/1981 | Auth et al. | 128/303.1 |
| 4,676,231 | 6/1987 | Hisazami et al. | 606/14 |
| 4,693,244 | 9/1987 | Daikuzono | 128/398 |
| 4,693,556 | 9/1987 | McCaughan | 606/15 |
| 4,736,743 | 4/1988 | Daikuzono | 128/303.1 |
| 4,799,479 | 1/1989 | Spears | 128/303.1 |
| 4,832,979 | 5/1989 | Hoshino | 128/303.1 |
| 4,848,339 | 7/1989 | Rink et al. | 128/398 |
| 4,860,743 | 8/1989 | Abela | 606/15 |
| 4,878,492 | 11/1989 | Sinofsky et al. | 128/395 |
| 4,994,060 | 2/1991 | Rink et al. | 606/28 |

FOREIGN PATENT DOCUMENTS 63-216579 8/1988 Japan .
2185188 7/1987 United Kingdom .

OTHER PUBLICATIONS

Suzuki et al., "Endoscopic local hyperthermia with Nd-YAG laser –experimental study and development of computed thermo-system", *Bulletin of the Japan Society of Laser Medicine*, vol. 6, No. 3, Jan. 1986, pp. 347–350.

*Primary Examiner*—Max Hindenburg
*Attorney, Agent, or Firm*—Lowe, Price, LeBlanc & Becker

[57] ABSTRACT

A laser light emitting probe used in a medical treatment. It has longitudinally a base end to impinge on, a body to penetrate through and a tip end to emit from for laser light, comprising the tip end being covered with a light scattering surface and bending at a certain angle on a longitudinal cross section. Preferably, the tip end is covered with a surface layer containing laser light absorbing particles and laser light scattering particles having a larger refractive index than that of the material of the probe on the surface of at least from the bending part to the end part of the tip end. A producing method of the probe comprising tapering a laser light transmissable member at least at a tip end thereof, bending the transmissible member at the tip end, making contact the transmissible member with a dispersion including at least said two kinds of particles and laser light transmissible particles having a melting point not higher than that of the transmissible member, and baking the transmissible member at a temperature higher than the melting point of said transmissible particles and within a limit as transmissible member can keep its shape.

23 Claims, 6 Drawing Sheets

BENT AND TAPERED LASER LIGHT EMITTING PROBE

BACKGROUND OF THE INVENTION

This invention relates to a laser light emitting probe to permit an incision, a vaporization of living tissue of animal organisms or a thermal therapy, and the producing method of said laser light emitting probe.

Medical treatments such as incisions of living tissue of animal organisms by irradiation with laser light are conspicuous due to its ability of hemostasis in these days. It had been the conventional method that the laser light was irradiated from the fore end of an optical fiber system which is non-contact with the living tissue. But this method causes severe damage to the fore end of the optical fiber system. Therefore, a method which has been utilized lately is as follows; at first, the laser light, after being transmitted into an optical fiber system, is fed into an emitting member of a probe being in contact or non-contact with the living tissue (hereafter "living tissue" is sometimes expressed by "tissue" only). Then the laser light emitted from the surface of the probe is irradiated on the tissue.

Figure 11:
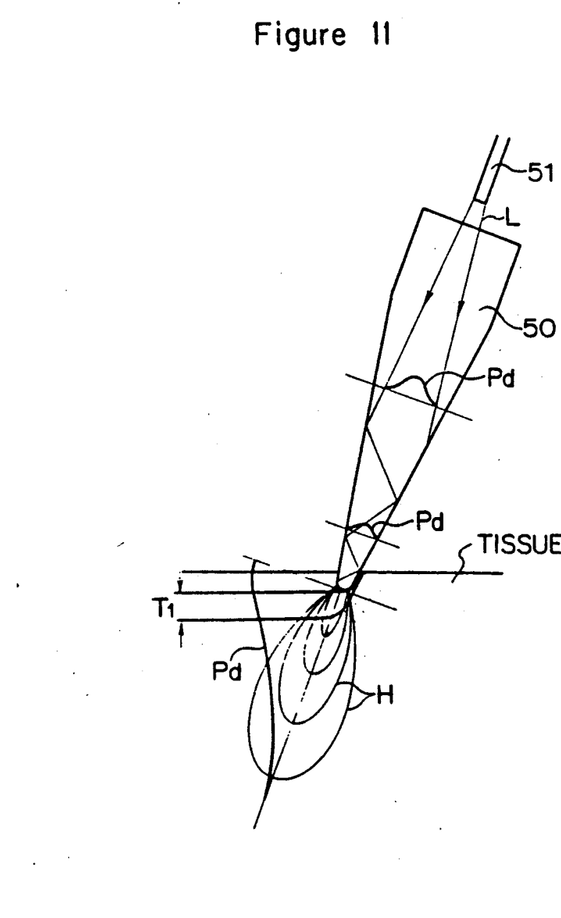
FIGS. 11 and 12 are schematic illustrations showing embodiments and power density distribution diagrams of the laser light of probes earlier developed by the inventor.

The inventor developed many kinds of contact probes which are utilized for various purposes. One embodiment is shown in FIG. 11. This probe is made of sapphire, quartz and the like. Usually, it has a smooth surface and does not have a surface layer. Further, it has a tip end of a tapered conical shape.

Referring to FIG. 11, laser light L is fed by means of an optical fiber 51 into the probe 50, which is of long and narrow conical shape with a round tip end and whose outer surface is smooth. The laser light L passing through the probe 50 is reflected and refracted on an inner surface to reach the tip end, finally is emitted only from the tip end.

In this case, a power density and its distribution of the laser light L are shown as contour lines H and a curve Pd respectively in FIG. 11. Accordingly, it is obvious that the laser light L is concentratedly emitted from the tip end of the probe 50. Therefore, while the thickness (depth) T1 of a coagulation layer C is increased, the laser light does not irradiate effectively to tissue along the side of the probe, then the effect of an incision and hemostasis at the tissue along the side of the probe is reduced. As a result, in case of the incision of hemorrhagic tissue such as liver and the like, the probe must be repeatedly moved along the same incision line little by little. Therefore, the surgery requires much labour and must be done carefully.

Under these circumstances, the inventor found a surface treatment method for the probe; formation a roughened surface of the probe extends the effective area of laser light irradiation, because the laser light is refracted on the roughened surface to be emitted in many directions.

Although it is possible to extend the effective area of the laser light irradiation by means of the above method, its efficiency is not sufficient. In order to compensate the low efficiency of the incision for the tissue along the side of the probe, an output power level from a laser light generator should be enhanced. Further, the high power level laser light causes a severe damage to the tissue. Therefore, this probe is not applicable for the incision of hemorrhagic internal organs.

The inventor had done a lot of research on these defects to find the following.

The effect of the incision at a side part of the incised portion is enhanced by a formation of a rough outer surface of the probe covered with a surface layer having laser light scattering particles. Because, a scattering effect is extended by means of the light scattering particles in the surface layer as well as the roughened surface of the probe.

Figure 12:
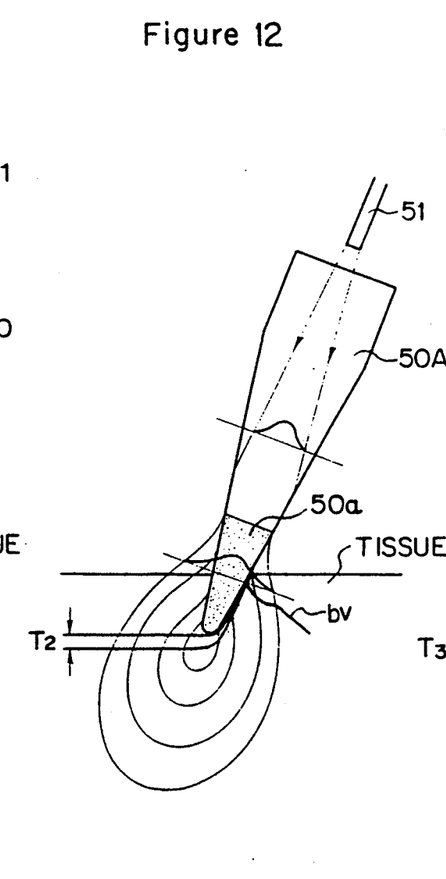

Referring to FIG. 12, by a probe 50A having said surface layer 50a, a broad laser light irradiation pattern can be obtained, while a depth T2 of a coagulation layer is reduced. Accordingly, the effect of the incision at the side part of the incised tissue is enhanced.

However, some defects still exist in said probe. The first defect relates to hemostasis. Since the laser light is emitted from the tip end more than from the side of the probe, the coagulation layer in the tissue at the side part of the probe is not so deep. Therefore, the effect of the hemostasis shown by the depth of the coagulation is known to be reduced. If there is a blood vessel adjacent to the thin coagulation at the side part of the probe, bleeding is apt to be caused.

The second defect relates to the process of the incision. When the probe starts to move along an incision line, the tissue is incised by the tip end of the probe. Therefore, it is comparatively easy for the probe to move on the surface of the tissue. There remains, however, a difficulty of the probe movement in the tissue at the side part of the probe. In other words, it is easy to start to incise, but it is difficult to continue to incise along the incision line.

Another defect is that it is also difficult to know an incised depth in the tissue, because the probe moves too easily on the surface of the tissue.

On the other hand, such consideration for the hemostasis must not be taken for the incision of less hemorrhagic tissue such as skin, fat layer and the like. In order to compensate the reduced effect of the incision at the side part of the incised tissue, however a high laser power is required. This causes a damage to the tissue. Further, this necessitates a high power and expensive laser light generator. If the laser power remains at a low level, the probe must be moved slowly. Then, a surgery using this probe can not be carried out quickly.

OBJECTS OF THE INVENTION

It is an object of the present invention to provide a laser light emitting probe having a large effective area of laser light irradiation and high efficiency of an incision by tissue vaporization and of hemostasis at a side part of incised tissue.

It is another object of the present invention to provide a laser light emitting probe requiring a low power level of laser light in case of an incision for less hemorrhagic tissue.

It is another object of the present invention to provide a laser light emitting probe which can be moved quickly in case of an incision for hemorrhagic and also for less hemorrhagic tissue.

It is another object of the present invention to provide a laser light emitting probe which can be operated easily in case of an incision.

It is another object of the present invention to provide a producing method of the laser light emitting probe.

Other and further objects, features and advantages of the present invention will appear more fully from the following description.

SUMMARY OF THE INVENTION

The present invention features a laser light emitting probe having longitudinally a base end to impinge on, a body to penetrate through and a tip end to emit from for laser light, comprising the tip end being covered with a light scattering surface and bending at a certain angle on a longitudinal cross section.

In the preferable embodiment of the present invention, the angle made by a center line of a non-bending portion and a normal line to a tangent line of an externally swelled surface of the bending part of the tip end is larger than a critical angle of the material of the probe to the air.

In another preferred embodiment of the present invention, said bending tip end is tapered.

In another preferred embodiment of the present invention, the probe is covered with a surface layer containing laser light absorbing particles and laser light scattering particles having a larger refractive index than that of the material of the probe on the surface of at least from the bending part to the end part of said bending tip end.

In another preferred embodiment of the present invention, the surface layer contains said two kinds of particles and a binder made from a laser light transmissible material.

In another preferred embodiment of the present, the surface of said bending tip end of the probe is roughened and said surface layer is formed on said roughened surface.

In another preferred embodiment of the present invention, an externally swelled surface of said bending tip end is tapered towards an external side on a cross section.

The present invention further features a producing method of the laser light emitting probe comprising the steps of:
(a) tapering a laser light transmissible member at least at the tip end,
(b) bending said transmissible member at the tip end at a certain angle on a longitudinal cross section,
(c) making contact said transmissible member with a dispersion including at least said two kinds of the particles and laser light transmissible particles which have melting point same to or lower than that of the transmissible member, and
(d) baking said transmissible member with the dispersion at a temperature which is higher than the melting point of said laser light transmissible particles and within a limit as the transmissible member can keep its shape.

DETAILED DESCRIPTION OF THE INVENTION

According to the present invention, covering a laser light scattering surface on a tip end of a probe enhances a laser light irradiation pattern. Because, laser light penetrated through in the probe is scattered at the surface of the probe, then laser light power emitted from the tip end of the probe is reduced while the laser light power from the side surface of the probe is increased. Further, said probe has the tip end bending at a certain angle on a longitudinal section, then the laser light power is concentrated at the externally swelled side part of the bending tip end more than at the inner side part thereof where there is a curvature center of the bending and the laser light having large power is irradiated from the side surface of the probe to tissue as shown in the distribution diagram of FIG. 4. Therefore, a vaporization of the tissue to be incised at the side part of the probe is accelerated to facilitate the incision for this tissue. Further, as a depth of a coagulation layer made by the incision is increased, hemorrhagic tissue can be incised without much bleeding.

Figure 5:
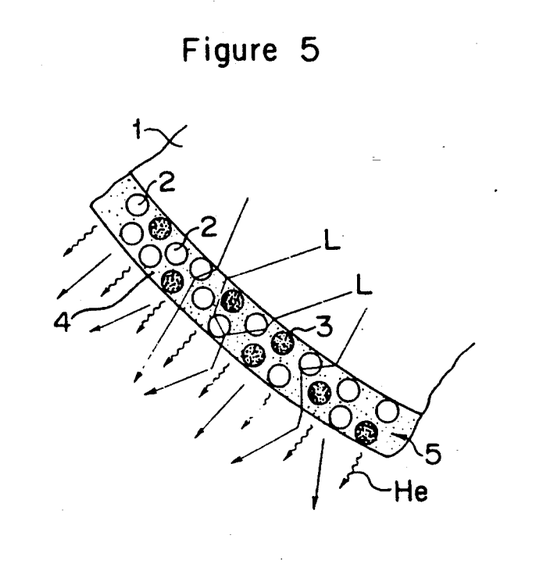
FIGS. 5 and 6 are enlarged sectional views of surface layers.

As shown in FIG. 5, instead of forming a light scattering surface on a laser light transmissible member only by roughening, a surface layer 5 can be formed on a surface of a transmissible member 1. Hereupon, the surface layer 5 contains light scattering particles 2 made of sapphire and the like having a larger refractive index than that of the transmissible member 1. While laser light L emitted from the transmissible member 1 passes through the surface layer 5, the laser light L, which impinges on the light scattering particle 2, is partially reflected on the surface of the light scattering particle 2, or partially penetrates into and is emitted from the particle 2 with refraction. Therefore, the laser light L is emitted in various directions from the entire surface layer 5. As a result, forming said surface layer 5 produces an area of laser light irradiation larger than an area of laser light irradiation in case of forming the light scattering surface only by roughening.

Further, the surface layer 5 preferably contains laser light absorbing particles 3 made of carbon and the like. Accordingly, when the laser light L impinges on the laser light absorbing particle 3, the greater part of the energy of the laser light L is converted to heat energy He by means of the laser light absorbing particle 3, and the tissue is heated by the heat energy He from the surface layer 5.

By so doing, as the vaporization of the tissue is accelerated, the tissue can be incised with low energy of the laser light penetrated into the transmissible member 1. Therefore, when the tissue is incised, the transmissible member 1 can be moved rapidly. Further, the required energy of the laser light penetrating into the transmissible member 1 is low. As a result, the surgery can be carried out in short time, and with a cheap and small scaled laser light generator.

Preferably, the surface of the transmissible member 1 is roughened, then this rough surface of the transmissible member is covered with said surface layer in order to obtain a sufficient effect of the laser light scattering.

On the other hand, referring to the surface layer, for example, if a dispersion containing said laser light absorbing particles and light scattering particles is coated on the surface of the transmissible member, after a vaporization of a dispersion medium, X the contact of the probe having the surface layer with the tissue or other substances causes a damage to the surface layer X, because both kinds of particles are attached to the surface of the transmissible member only by physical adsorptive power.

By using a binder which sticks the laser light absorbing particles and the light scattering particles to the surface of the transmissible member, adhesion of the surface layer to the transmissible members is extended.

In this case, the binder is preferably made of light transmissible material 4 such as quartz and the like to ensure the emission of the laser light from the surface layer 5. On the other hand, laser light transmissible particles having a melting point the same as or lower than that of said transmissible member 1 are used as the transmissible material 4 and they are dispersed together with said absorbing particles and said light scattering particles in a proper liquid such as water. Then the transmissible member 1 painted with this dispersion is baked at a temperature which is higher than a melting point of the transmissible particle and within a limit as the transmissible member can keep its shape. Accordingly, the transmissible particles melt to form the surface layer of high mechanical strength together with the laser light absorbing particles and the light scattering particles. Therefore, the damages to the surface layer can be reduced because of its high strength.

Now, the present invention is described more particularly.

Figure 3:
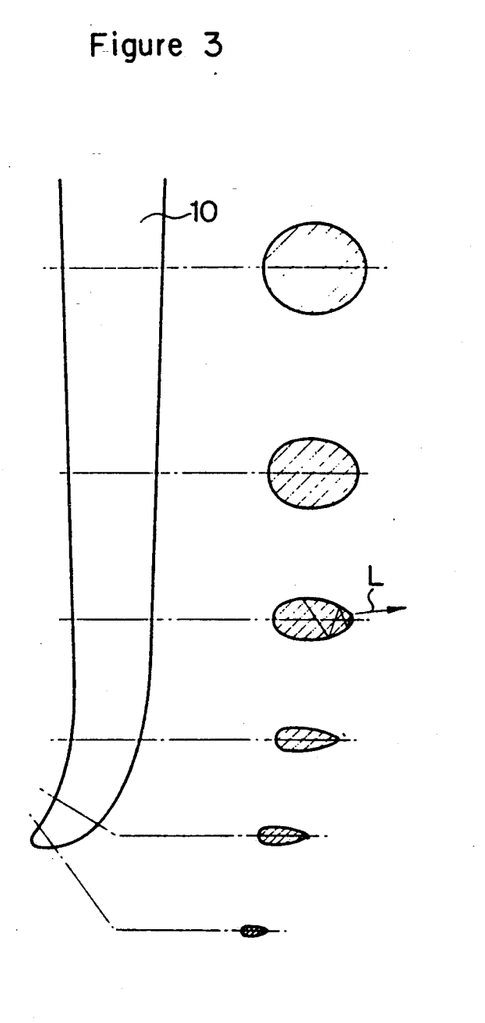

FIG. 5 is an enlarged sectional view of the surface layer 5 of a probe 10, an example of whose end tip is shown in FIG. 3. On the transmissible member 1, the surface layer 5 containing the laser light scattering particles 2 and laser light absorbing particles 3 is formed with the laser light transmissible material 4 which is melted to be the binder as described before.

Figure 6:
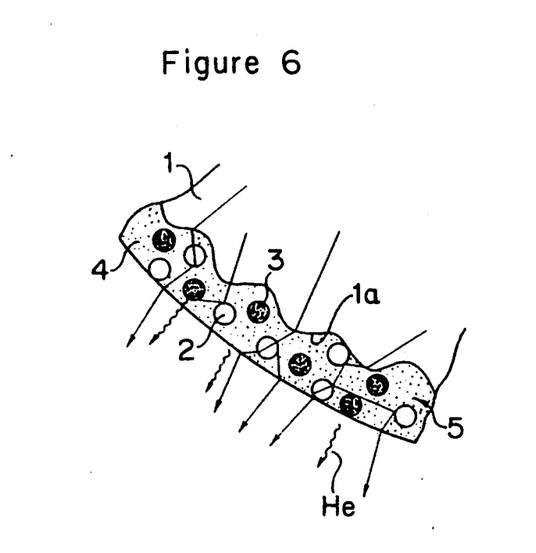
Figure 7:
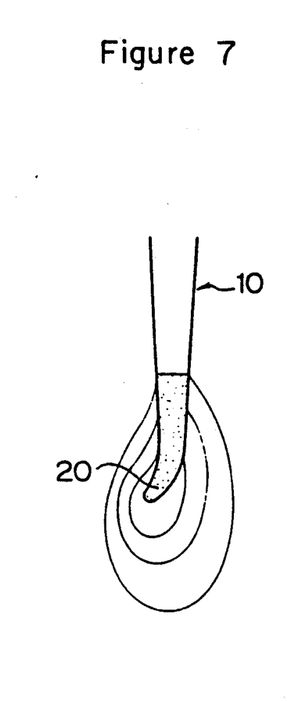
FIGS. 7, 8, 9 and 10 are power density distribution diagrams of laser light, wherein each tip end of the probe bends at a different angle.
Figure 8:
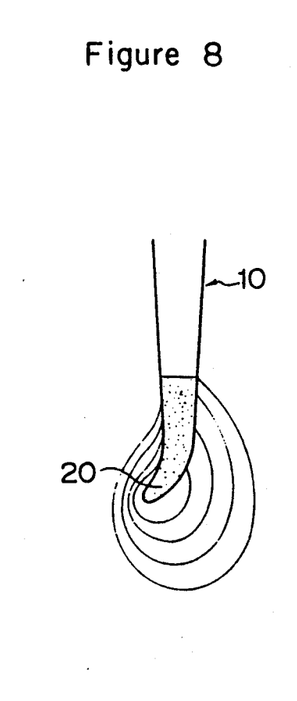
Figure 9:
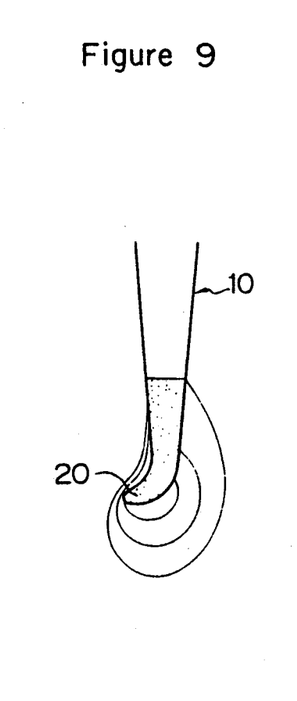
Figure 10:
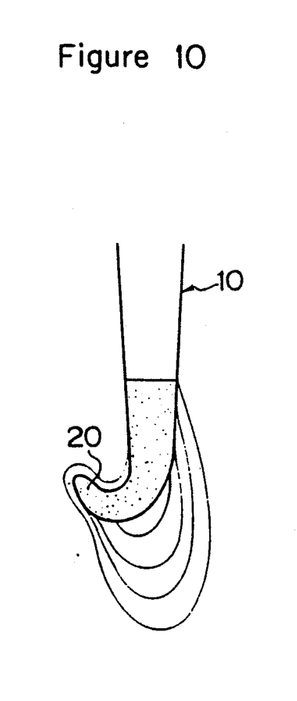

In this case, forming of rough surface 1a on the transmissible member 1, shown in FIG. 6, enhances a scattering effect of the laser light.

Figure 1:
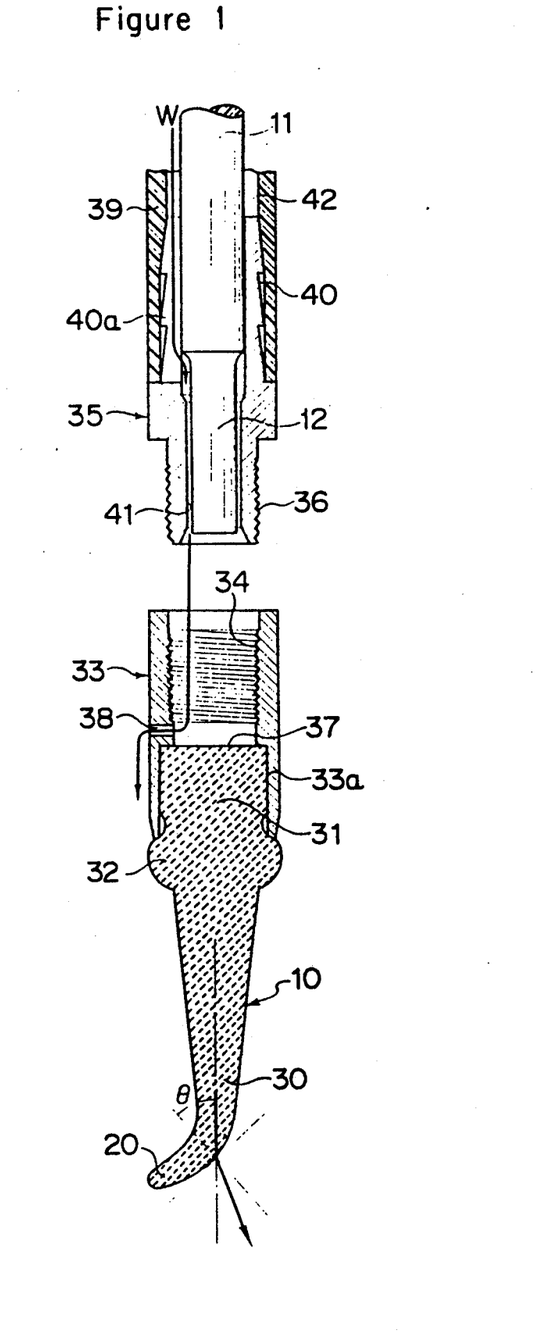
FIG. 1 is a longitudinal sectional view of a structure of a probe and a holding member therefor relating to the present invention.

An example of the structure of said probe 10 and a holding member therefore is shown in FIG. 1.

This probe 10 comprises a conically tapered inserting portion 30, a main holding portion 31, a flange 32 formed between them, and bending tip end 20. The main holding portion 31 of the probe 10 is fitted in a cylindrical female connector 33 and fixed integrally thereto by caulking the mating portions 33a, by using a ceramic type adhesive between the mating surfaces or by the combination of these both means. The female connector 33 has, on the internal surface thereof and further in a side part of a base end of the probe 10, a female thread 34 which is adapted to mate removably with a male thread 36 of a male connector 35. The female connector 33 has holes 38 which facilitates the passage of cooling water W inside and outside thereof. The holes 38 are disposed adjacent to the top of a light receiving base 37 of the probe 10, for example, oppositely on a circumference of the female connector 33 although only one of them is shown in FIG. 1.

On the other hand, the male connector 35 is pressed to be fitted into an end portion of a flexible tube jacket 39 fabricated of, for example, Teflon (the trademark for polytetrafluoroethylene). For this press fitting, the male connector 35 has stepped portions 40 at its base portion, and is firmly held so as to prevent the male connector 35 being disengaged from the tube jacket 39.

A transmitting optical fiber 11 for the laser light attached by an optical fiber 12 is inserted in the tube jacket 39 and the male connector 35. There is a gap 42 between the optical fiber 11 and the tube jacket 39 for passage of cooling water. The end portion of the transmitting optical fiber 11 is closely fitted in the male connector 35 at its stepped portion 40, however, the stepped portion 40 has, for example, two slits 40a formed oppositely on a circumference of the stepped portion 40 for the cooling water W. The cooling water W is passed through the slits 40a and a passage 41 provided between the inner surface of the end portion of the male connector 35 and the outer surface of the transmitting optical fiber 11.

A tip end for emitting the laser light having above described structure is equipped in an endoscope and some other suitable holders while the female connector 33 is connected to mate with the male connector 35. Alternatively, the female connector 33 attached by the probe 10 is equipped directly in some suitable holders which already has the transmitting optical fiber 11.

In this way, a pulse laser light such as YAG and the like introduced through the optical fiber 12 penetrates the probe 10 from the light receiving base 37, therefore, is emitted mainly from all over the outer surface of the bending tip end 20. At the same time, the cooling water W is fed through a gap 42, the slit 40a, a gap 41 to cool the probe 10, further, discharged through the opening 38 to flow out on the surface of tissue and then cool the tissue.

The transmissible member of this invention is preferably fabricated from a natural or artificial ceramic material such as diamond, sapphire, quartz and the like due to their heat resistance.

The light scattering particles relating to the present invention, having a larger refractive index for the laser light than that of the transmissible member are of a natural or artificial material such as diamond, sapphire, quartz (a melting point is preferably high), single crystal zirconium oxide ($ZrO_2$), high melting point glass, transmissible and heat resistant synthetic resin, laser light reflective metal such as gold or aluminium, and a particle which is laser light reflective or non-reflective metal particle coated with laser reflective metal such as gold, aluminum and the like by means of the surface treatment such as gilding.

The laser transmissible material is preferably made of the transmissible particle which can make a film when it melts, and is more preferably heat resistant such as a natural or artificial, sapphire, quartz, glass, transmissible and heat resistant synthetic resin and the like. A suitable transmissible material is selected from these materials in consideration of the relation to the material of the transmissible member.

The laser light absorbing particle is made of carbon, graphite, iron oxide, manganese dioxide and the any other materials which can absorb the laser light to generate heat energy.

A content of each particle in the surface layer(wt %) and each average particle size is preferably within ranges as shown in a following table. More preferably each content and particle size are put in parentheses.

|  | Content (wt %) | Average Particle Size (μm) |
| --- | --- | --- |
| Light Scattering Particle (A) | 90-1 (70-20) | 0.2-300 (1-50) |
| Transmissible Particle (B) | 10-90 (20-50) | 0.2-500 |
| Absorbing Particle (C) | 90-1 (70-10) | 0.2-500 (1-100) |

The thickness of the surface layer is preferably 10 μm-5 mm, more preferably 30 μm-1 mm. The surface layer is formed by the following methods. If the surface layer can not be formed to be a desired thickness by one step of the method, the step should be repeated until the desired thickness can be obtained;

Said three kinds of particles are dispersed in a dispersion medium, then it is heated to a temperature which is higher than a melting point of the transmissible particles, and the transmissible member is dipped in the dispersion.

Alternatively said three kinds of particles are melted to be sprayed to the transmissible member simultaneously.

Further, other suitable methods for forming the surface layer can be used.

Hereupon, by the above described first method, the dispersion dispersing said three kinds of particles can be painted to the transmissible member. Moreover, this painting method facilitates the operation, because only the part desired to be the surface layer of the transmissible member, or preferably only the part desired to be the bending part of the tip end, necessitates being dipped in the dispersion and pulled up therefrom. Therefore this method is practical and rational.

As the dispersion medium, suitable liquid for example, water, alcohol or mixture of them can be used. Further sugar or starch is added to increase the viscosity of the dispersion medium.

Figure 4:
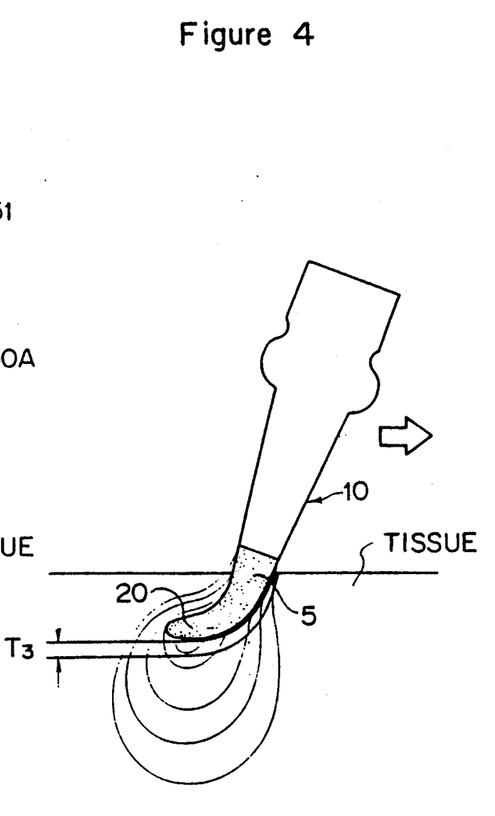
FIG. 4 is a schematic illustration showing an embodiment of a laser light emitting probe for a laser scalpel and a power density distribution diagram of laser light in this embodiment.

As described before, according to the present invention, the forming of the surface layer 5 on the surface of the transmissible member 1 extends the area of the tissue irradiated by the laser light. Because the laser light is emitted widely in many directions from the surface layer 5 as shown in FIG. 4.

Figure 13:
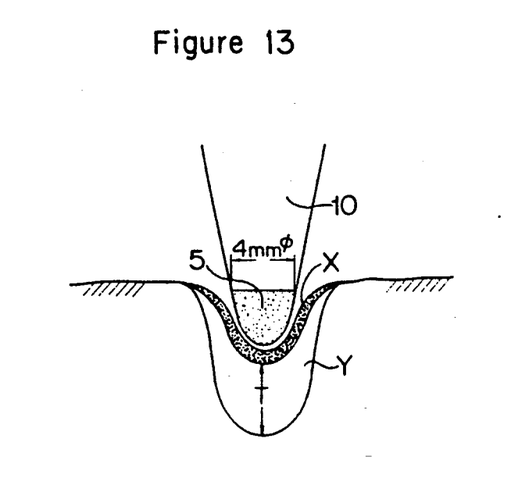
FIG. 13 is a schematic illustration explaining an experiment relating to the present invention.
Figure 14:
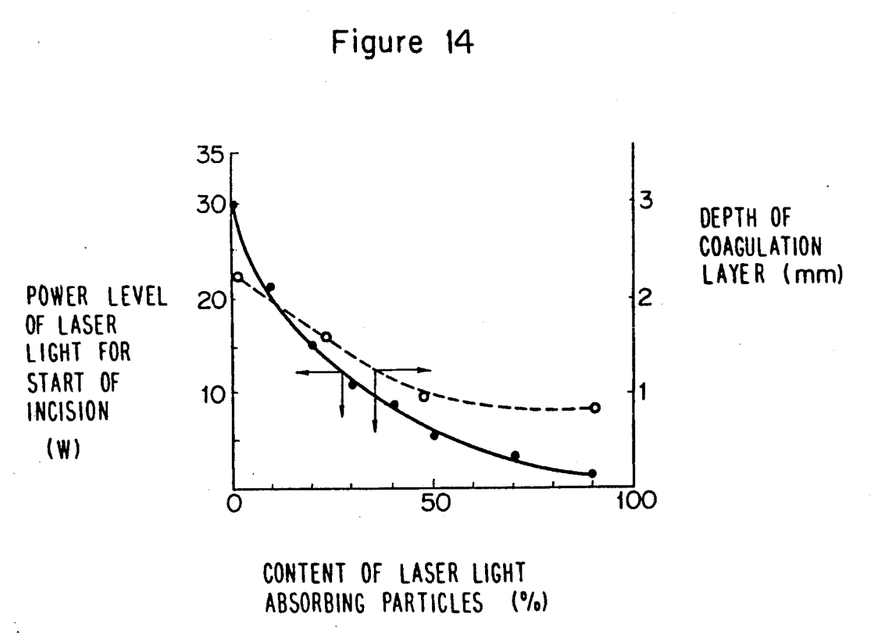
FIG. 14 is a graph showing the result of said experiment illustrated in FIG. 13.

On the other hand, the inventor used a probe which is not bending but straight shaped as shown in FIG. 13 for the experiment mentioned below;

In the following section, contents of the light scattering particle, the transmissible particle, and the laser light absorbing particle will be referred as (A), (B) and (C) respectively. The inventor investigated each change of following two parameters against (C) under fixed condition of (A):(B)=2:1. One investigated parameter is the laser light power level with which an incision to a pig's liver can be started. Another is a depth T of a coagulation layer Y below a carbonized layer X. Then, the result in FIG. 14 is obtained.

According to this result, when percentage of (C) is high, the incision can be started with a low power level of the laser light, then it is possible for the probe to be moved quickly. Hemostasis of the treated tissue around the tip end of the probe however, is known to be reduced as the reducing of the depth T of the coagulation layer $Y_X$, because the effect of hemostasis is dependent on the depth of the coagulation layer. Therefore, the probe with high percentage of (C) in the surface layer turns out to be used effectively for the incision to the tissue which bear the damage to some extent such as skin, fat layer and the like.

On the other hand, the probe with low percentage of (C) turns out to be useful to incise the tissue for which the hemostasis is regarded to be important such as liver, heart and the like. In this case, it is also clear that the power level of the output from the laser light generator must be raised and the probe must be moved slowly.

Referring to the above described experiment, the inventor introduced these two equations, (1) and (2).

$$\frac{(C)}{(A)+(B)+(C)} \propto \frac{\text{Quantity of laser light for heating}}{\text{Incident laser energy}} \quad (1)$$

$$\frac{(A)+(B)}{(A)+(B)+(C)} \propto \frac{\text{Quantity of laser light for transmitting}}{\text{Incident laser energy}} \quad (2)$$

Equation (1) means that heat generation is progressed as (C) is increased, then the incision is carried by mainly evaporation. Therefore, the laser light can not penetrate so deeply into the tissue because most of the incident laser light energy is spent for the heating. As a result, since the incidence of the laser light is not deep in the tissue, the depth of the coagulation layer is reduced.

Equation (2) means that a lot of impinging laser light energy penetrates deeply into the tissue as (C) is decreased, then the tissue absorbing laser light is heated, therefore, the coagulation is made in the tissue.

If some kinds of probes having different percentage of (C) in the surface layers are prepared in advance, a suitable probe can be selected in accordance with a medical purpose, thereby a suitable treatment can be carried out.

Although the probe in the present invention must be covered with the light scattered surface, said surface layer is not necessary. It may be a probe of which surface is roughened only.

However, the probe in the present invention must have the tip end which bends at a certain angle on a longitudinal section. Hereupon the meaning of "bending" includes bending as making an angle straightly as well as bending as making a curvedness.

A power density distribution of the laser light changes as a bending angle changes as shown in FIGS. 7, 8, 9 and 10. Increasing the bending angle extends the rate of the laser light power emitted from the side surface of the probe. Here, the bending angle θ is an angle made by a center line of a non-bending portion and a normal line to a tangent line of an externally swelled surface of the bending part of the tip end on the longitudinal section, which is shown in FIG. 1. The angle θ is preferably larger than a critical angle of the material of the probe (the transmissible member) to the air, in order to obtain a sufficient effect of the laser light scattering from the side surface of the probe.

When a thickness of the bending tip end is uniform, the laser light emitted from the end part of the bending tip end is increased while that from the side surface of the probe is decreased. Therefore, the bending tip end is preferably tapered.

In the embodiment of FIG. 3, the tip bends or curves around in a first direction, e.g. to the left in this drawing figure. The cross section of the bent portion also tapers or narrows in a direction away from the direction of the bend, e.g. to the right of FIG. 3. The wider areas to the left of the cross section would be on the interior of the bend in the tip, and the narrow edge of the taper is on the exterior side of the bend.

Figure 2:
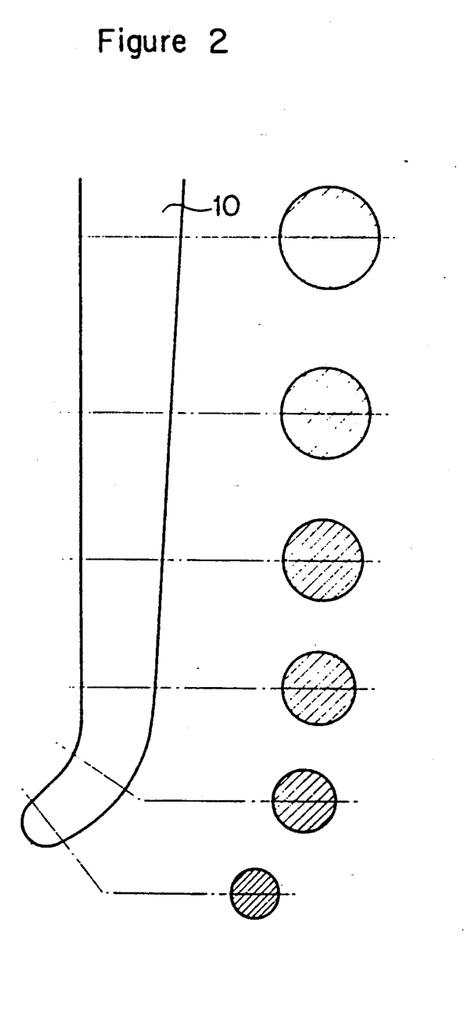
FIGS. 2 and 3 are schematic enlarged front views and enlarged sectional views of laser light emitting probes relating to the present invention.

If the cross section of the probe is a circle as shown in FIG. 2, the laser light emitted from the circumference is substantially uniform. However, as shown in FIG. 3, if the externally swelled side of the bending tip end is tapered towards an external side (to the right or lower right on FIG. 3), the laser light emitted to the external side is increased. This is obvious from the illustration of a course of the laser light in FIG. 3. As a result, the incision is carried much easily. Moreover, the probe which is sharp-edged towards the external side facilitates a mechanical incision as well as the incision by the laser light. As a result, an effect of the incision is significantly enhanced.

An example of producing method of the probe having above described shape is explained in the following;

At first, heat a conically tapered probe to a temperature higher than a softening temperature of the probe.

Bend at only the part of the tip end of the probe at a certain angle on a longitudinal section.

Press a part of an externally swelled side of the bending tip end from both before and back outer surfaces of the tip end on a cross section. Then the above described probe is obtained.

If the surface of the probe is covered with said surface layer, the characteristics of the probe described before becomes outstanding.

The shape of the probe base of the present invention is not limited to the cylindrical shape shown in FIGS. 1 and 4. It may be other shapes such as tapered cone, prism and the like.

What is claimed is:

1. A laser light emitting member comprising:
   a light transmissible member having a base end on which laser light is received, a body coupled with said base end through which said laser light penetrates and a tip end coupled to said body for emitting said laser light; and
   a laser light scattering surface layer covering said tip end; wherein
   a portion of said tip end bends in a first direction at a certain angle such that at least a portion of the laser light is emitted from a surface of the bent portion of said tip end on the external side of the bend, and
   the external surface of said bent portion of the tip end tapers in a second direction away from said first direction.

2. A laser light emitting member as claimed in claim 1, wherein:
   said certain angle is defined by a center line of a non-bending portion and a line normal to a tangent of the external surface of the bent portion of the tip end; and
   said certain angle is larger than a critical angle of the material of the light transmissible member to the air, such that laser light transmitted along or parallel to the center line will pass through the external surface of said bent portion of the tip end.

3. A laser light emitting member as claimed in claim 1 wherein the bent portion of tip end is tapered.

4. A laser light emitting member comprising:
   a base end on which laser light is received,
   a body coupled with said base end through which said laser light penetrates,
   a tip end coupled to said body for emitting said laser light, said tip end comprising a portion bent in a first direction at a certain angle, wherein a surface of said bent portion of the tip end forms a taper in a direction away from the first direction, the laser light being emitted from the tapered surface of the bent portion of said tip end with the highest concentration of the emitted light emerging from the narrowest part of the taper; and
   a surface layer covering at least said bent portion of said tip end, said surface layer containing laser light absorbing particles and laser light scattering particles having a larger refractive index than that of the material of the member.

5. A laser light emitting member as claimed in claim 4, wherein said surface layer further contains a binder made from a laser light transmissible material.

6. A laser light emitting member as in claim 5, wherein said laser light absorbing particles comprise particles of a first composition, said laser light scattering particles comprise particles of a second composition, wherein said first and second compositions are different form each other and from said laser light transmissible material.

7. A laser light emitting member as claimed in claim 4, wherein a surface of at least said bent portion of the tip end is roughened, and said surface layer is formed on said roughened surface.

8. A laser light emitting member as in claim 4, wherein said laser light absorbing particles comprise particles of a first composition and said laser light scattering particles comprise particles of a second composition different form said first composition.

9. A laser light emitting member as claimed in claim 4, wherein:
   said certain angle is defined by a center line of the body and a line normal to a tangent of a surface on the external side of the bent portion of the tip end; and
   said certain angle is larger than a critical angle of the material of the light transmissible member to the air such that at least a portion of the laser light transmitted along or parallel to the center line is emitted from a surface of the bent portion of said tip end.

10. A laser light emitting element comprising:
    a member comprising a laser light transmissible material, said member having a portion bent in a first direction at a certain angle such that at least a portion of laser light passing through said member is emitted from a surface of the bent portion on the external side of the bend, wherein the external surface of the bent portion of the tip end forms a taper in a direction away from the first direction.

11. A laser light emitting element as in claim 10, further comprising:
    a surface layer covering at least the surface of said bent portion of said laser light transmissible member;
    wherein said surface layer contains particles of a first type which absorb laser light, and particles of a second type which scatter laser light, said second type of particles being different from said first type of particles.

12. A laser light emitting element as in claim 11, wherein said surface layer further contains particles of a third type which are transmissive to laser light and act as a binder for the particles of the first and second types, said third type of particles being different from said first type of particles and said second type of particles.

13. A laser light emitting element as in claim 1, wherein:
said certain angle is defined by a center line of a non-bending portion of the element and a line normal to a tangent of the external surface of the bent portion of the tip end; and
said certain angle is larger than a critical angle of the material of the light transmissible member to the air, such that laser light transmitted along or parallel to the center line will pass through the external surface of the bent portion of tip end.

14. An element for contact laser surgery, said element comprising:
a light transmissible member through which laser light passes during surgery, said member having a portion for contact with tissue to be treated during surgery; wherein
the contact portion of said laser light transmissible member is bent at a certain angle such that at least a portion of the laser light is emitted from the contact portion of said laser light transmissible member, and
said contact portion of said laser light transmissible member is tapered to narrow toward the external side of the bend in the contact portion of said laser light transmissible member.

15. An element for contact laser surgery as in claim 14, wherein said external side forms a sharp edge.

16. An element for contact laser surgery as in claim 14, wherein said light transmissible member is tapered with decreasing size of the taper continuing through the bent contact portion of said laser light transmissible member.

17. An element for contact laser surgery as in claim 14, further comprising:
a surface layer covering at least the surface of said contact portion of said laser light transmissible member;
wherein said surface layer contains particles of a first type which absorb laser light, and particles of a second type which scatter laser light, said second type of particles being different from said first type of particles.

18. An element for contact laser surgery as in claim 17, wherein said surface layer further contains particles of a third type which are transmissive to laser light and act as a binder for the particles of the first and second types, said third type of particles being different from said first type of particles and said second type of particles.

19. An element for contact laser surgery as claimed in 14, wherein:
said certain angle is defined by a center line of a non-bending portion of the member and a line normal to a tangent of an external surface of the bent portion of the tip end; and
said certain angle is larger than a critical angle of the material of the light transmissible member to the air, such that laser light transmitted along or parallel to the center line will pass through the external surface of the bent portion of tip end.

20. A method of irradiating tissue comprising the steps of:
passing light from a laser through a transparent member;
emitting said laser light from a portion of said transparent member which bends at an angle permitting light emission and tapers so as to narrow and concentrate light toward the exterior side of the bend;
contacting the tissue to be irradiated with said bend of said transparent member; and thereby
applying the light emitted from the bend of said transparent member to the tissue.

21. A method of irradiating tissue as in claim 20 further comprising the steps of:
absorbing a portion of the laser light emitted from the bend of the transparent member in first particles contained in a surface layer on the bend of the transparent member, said absorbing converting said portion of laser light to heat;
scattering another portion of the laser light emitted from the bend of the transparent member off second particles contained in said surface layer on the bend of the transparent member, wherein the second particles are different from the first particles.

22. A method of irradiating tissue as in claim 21 wherein the second particles have a refractive index greater than the refractive index of the member.

23. A method of irradiating tissue as in claim 21 further comprising the step of passing a third portion of the emitted from the bend of the transparent member through a light transmissible binder contained in said surface layer.

* * * * *